United States Patent
Ikeda

(10) Patent No.: US 12,220,116 B2
(45) Date of Patent: Feb. 11, 2025

(54) BLOOD VESSEL HARVESTING SYSTEM

(71) Applicant: Teikyo University, Tokyo (JP)

(72) Inventor: Tsukasa Ikeda, Tokyo (JP)

(73) Assignee: Teikyo University, Tokyo (JP)

( * ) Notice: Subject to any disclaimer, the term of this patent is extended or adjusted under 35 U.S.C. 154(b) by 906 days.

(21) Appl. No.: 17/299,550

(22) PCT Filed: Dec. 17, 2019

(86) PCT No.: PCT/JP2019/049296
§ 371 (c)(1),
(2) Date: Jun. 3, 2021

(87) PCT Pub. No.: WO2020/129943
PCT Pub. Date: Jun. 25, 2020

(65) Prior Publication Data
US 2022/0054116 A1    Feb. 24, 2022

(30) Foreign Application Priority Data

Dec. 19, 2018    (JP) ................................ 2018-237433

(51) Int. Cl.
*A61B 17/00*    (2006.01)
*A61B 1/00*    (2006.01)
(Continued)

(52) U.S. Cl.
CPC ...... *A61B 17/00008* (2013.01); *A61B 1/0005* (2013.01); *A61B 1/018* (2013.01);
(Continued)

(58) Field of Classification Search
CPC . A61B 17/00008; A61B 1/0005; A61B 1/018; A61B 1/3137; A61B 90/37;
(Continued)

(56) References Cited

U.S. PATENT DOCUMENTS 5,471,988 A    12/1995 Fujio
5,667,480 A    9/1997 Knight
(Continued)

FOREIGN PATENT DOCUMENTS

CN    101480350 A    7/2009
CN    102131467 A    7/2011
(Continued)

OTHER PUBLICATIONS

Windish R, Ungar T, Backlund B, Haukoos JS, Kendall J. Use of sterile saline as a conduction agent for ultrasound visualization of central venous structures. Emerg Med Australas. Jun. 2010;22(3):232-5. doi: 10.1111/j. 1742-6723.2010.01297.x. PMID: 20590784( abstract only) (Year: 2010).*

(Continued)

*Primary Examiner* — Sunita Reddy
(74) *Attorney, Agent, or Firm* — McDonnell Boehnen & Berghoff LLP

(57) ABSTRACT

A blood vessel harvesting system, which harvests blood vessels in a state of being covered by surrounding tissue, includes a separating device and a display device. The separating device includes a rod portion that is inserted into a living body, an optically transparent taper-shaped separating portion that is disposed at a distal end part of the rod portion, an endoscope portion that is disposed inside the rod portion and captures an endoscope image of an interior of the living body via the separating portion, and an ultrasound transceiver portion that is disposed on an outer peripheral surface of the rod portion, irradiates the interior of the living body with an ultrasonic wave, and receives a reflected wave from the interior of the living body. The display device matches a scale of the endoscope image with a scale of an ultrasound image acquired by the ultrasound transceiver portion and simultaneously displays the endoscope image (Continued)

and the ultrasound image side by side on the display screen, and the display device disposes the endoscope image and the ultrasound image on the display screen such that a point in the endoscope image indicating a predetermined position in the living body matches a point in the ultrasound image indicating the predetermined position on the display screen.

5 Claims, 9 Drawing Sheets

(51) Int. Cl.
    *A61B 1/018*     (2006.01)
    *A61B 1/313*     (2006.01)
    *A61B 90/00*     (2016.01)

(52) U.S. Cl.
    CPC ............ *A61B 1/3137* (2013.01); *A61B 90/37* (2016.02); *A61B 2017/00969* (2013.01); *A61B 2090/3784* (2016.02)

(58) Field of Classification Search
    CPC .. A61B 2017/00969; A61B 2090/3784; A61B 1/00174; A61B 8/0891; A61B 90/361; A61B 2017/00907; A61B 2090/364; A61B 8/12
    USPC .......................................................... 600/36
    See application file for complete search history.

(56) References Cited

U.S. PATENT DOCUMENTS

| | | | | |
|---|---|---|---|---|
| 5,697,897 | A * | 12/1997 | Buchholtz | A61N 7/022 |
| | | | | 600/439 |
| 5,725,479 | A | 3/1998 | Knight | |
| 6,469,230 | B1 | 10/2002 | Edwards | |
| 7,022,131 | B1 * | 4/2006 | Derowe | A61B 17/22012 |
| | | | | 623/1.11 |
| 2009/0024156 | A1 * | 1/2009 | Chin | A61B 17/3417 |
| | | | | 606/190 |
| 2009/0192519 | A1 | 7/2009 | Omori | |
| 2013/0226285 | A1 * | 8/2013 | Strommer | A61B 1/00154 |
| | | | | 623/1.23 |
| 2015/0164632 | A1 * | 6/2015 | Stewart | A61B 17/00008 |
| | | | | 600/36 |
| 2016/0157878 | A1 * | 6/2016 | Fujii | A61B 17/00008 |
| | | | | 606/167 |
| 2017/0189055 | A1 * | 7/2017 | Suehara | A61B 17/00008 |
| 2017/0245922 | A1 | 8/2017 | Fujii | |
| 2018/0000470 | A1 * | 1/2018 | Willis | A61B 1/00096 |
| 2018/0185007 | A1 * | 7/2018 | Andersen | A61B 1/31 |
| 2019/0099186 | A1 * | 4/2019 | Piskun | A61B 1/018 |
| 2019/0216489 | A1 * | 7/2019 | Lau | A61B 18/082 |

FOREIGN PATENT DOCUMENTS

| | | |
|---|---|---|
| CN | 103505288 A | 1/2014 |
| JP | 07227394 A | 8/1995 |
| JP | H09122133 A | 5/1997 |
| JP | 2000505315 A | 5/2000 |
| JP | 2005052667 A | 3/2005 |
| JP | 2009178230 A | 8/2009 |
| JP | 2011033725 A | 2/2011 |
| JP | 2017153600 A | 9/2017 |
| JP | 2017153606 A | 9/2017 |
| JP | 2018117975 A | 8/2018 |
| WO | 1997026831 | 7/1997 |
| WO | 2016027491 A1 | 2/2016 |
| WO | 2018051565 A1 | 3/2018 |

OTHER PUBLICATIONS

International Search Report for corresponding PCT application No. PCT/JP2019/049296 dated Feb. 25, 2020.

Japanese Office Action for corresponding application No. 2020-561440, dated Aug. 15, 2023.

Chinese Office Action for correspoding Chinese application No. 2019800832494 dated Jan. 8, 2024.

European Search Report for corresponding European Application No. 19899637.3-1126, dated Aug. 17, 2022.

* cited by examiner

BLOOD VESSEL HARVESTING SYSTEM

CROSS-REFERENCE TO RELATED APPLICATIONS

This application is a national stage application under 35 U.S.C. § 371 of International Application No. PCT/JP2019/049296, filed Dec. 17, 2019, which claims priority to Japanese Patent Application No. 2018-237433, filed Dec. 19, 2018, the contents of each of which are hereby incorporated by reference in their entirety.

TECHNICAL FIELD

The present invention relates to a blood vessel harvesting system.

BACKGROUND

A vein graft is a substitute blood vessel used in, for example, coronary artery bypass grafting, and as the vein graft, for example, a great saphenous vein graft (SVG) is used. As a method for harvesting a graft, there is a method (OVH: Open Vessel Harvesting) (first conventional method) in which skin is incised and a graft is harvested, which has been generally used so far. In addition, as another method for harvesting a graft, there is a method using an endoscope (EVH: Endoscopic Vessel Harvesting) (second conventional method). EVH has advantages such as fewer wound complications (wound infection, lymph fistula, or the like) and excellent cosmetology.

In the method using the current EVH device (second conventional method), the SVG is separated from a surrounding adipose tissue and only the SVG is harvested. In the method, for example, an operator of the EVH device first makes a small incision in the skin to secure the SVG directly underneath. Subsequently, the operator of the EVH device then separates, for example, the surrounding adipose tissue positioned on an upper side of the SVG from an upper part of an outer peripheral surface of the SVG by an optically transparent taper-shaped separator attached to a distal end part of the endoscope. In addition, the operator of the EVH device separates the surrounding adipose tissue positioned on a below side of the SVG from a lower part of the outer peripheral surface of the SVG. In addition, the operator of the EVH device separates the surrounding adipose tissue positioned on a left side of the SVG from a left part of the outer peripheral surface of the SVG. In addition, the operator of the EVH device separates the surrounding adipose tissue positioned on a right side of the SVG from a right part of the outer peripheral surface of the SVG. As a result, the SVG is in a state of hanging from the surrounding adipose tissue via a side branch extending radially from the outer peripheral surface of the SVG. Next, the operator of the dissection device inserts the dissection device into the living body in parallel with the endoscope, and executes side branch processing in which the side branch is dissected by the dissection device.

In the first conventional method and the second conventional method described above, since the SVG is harvested in an exposed state, the quality of the SVG, such as a graft patency rate, may be deteriorated due to graft damage and damage of an inner membrane associated with processing of expanding the graft by applying high pressure to the graft, which has been pointed out as a problem of the first conventional method and the second conventional method. Therefore, a no-touch method (pedicle method) in which the SVG is harvested in a state where the SVG (main trunk) is covered with the surrounding adipose tissue without touching the SVG may be used.

In the no-touch method, as described above, the SVG is harvested in a state where the SVG (main trunk) is covered with the surrounding adipose tissue without touching the SVG, and processing of expanding the vein by applying high pressure to the graft is also performed. As a result, damage to the vascular endothelium is reduced, an action of a vascular endothelial protective substance on the SVG from the surrounding adipose tissue is expected, and the graft patency rate is expected to be improved. On the other hand, the no-touch method has a problem in that there are many postoperative wound complications since the skin is incised.

Therefore, conventionally, the no-touch method by EVH has been tried. In the no-touch method by EVH at the current stage, the operator should use a conventional device to operate the endoscope based on an endoscope image in which the SVG is not visible and harvest the SVG in a state where the SVG (main trunk) is covered with the surrounding adipose tissue. In other words, the no-touch method by EVH at the current stage is considered quite difficult and difficult to use widely.

Further, conventionally, a separating device that harvests a blood vessel together with a surrounding tissue thereof is known (for example, refer to JP2017153606A). According to the technique disclosed in JP2017153606A, a separating device includes a grip portion that has an insertion lumen into which an imaging device (for example, an endoscope) can be inserted, and a separating member provided at a distal end part of the grip portion. The separating member has a separating portion provided with a processing unit that performs predetermined processing on a branched blood vessel (side branch) branched from the blood vessel, and a protruding portion protruding from the separating portion in the thickness direction of the separating portion.

However, in the technique described in JP2017153606A, for example, an endoscope image can be obtained by an imaging device, but a blood vessel is covered with a surrounding tissue. Therefore, the blood vessel does not appear in the image obtained by the imaging device, such as the endoscope image. Accordingly, the operator of the separating device disclosed in JP2017153606A should operate the separating device in a state where a position of the blood vessel cannot be grasped.

SUMMARY

In view of the above-described problems, an object of the present invention is to provide a blood vessel harvesting system capable of grasping a position of a blood vessel covered with a surrounding tissue when operating a separating device.

One aspect of the present invention is a blood vessel harvesting system that harvests a blood vessel in a state of being covered with a surrounding tissue, the blood vessel harvesting system including a separating device, and a display device, in which the separating device includes a rod portion that is inserted into a living body, an optically transparent taper-shaped separating portion that is disposed at a distal end part of the rod portion, an endoscope portion that is disposed inside the rod portion, and captures an endoscope image of an interior of the living body via the separating portion, and an ultrasound transceiver portion that is disposed on an outer peripheral surface of the rod portion, irradiates the interior of the living body with an ultrasonic wave, and receives a reflected wave from the interior of the living body, the display device includes a display screen on which the endoscope image and an ultrasound image generated based on the reflected wave received by the ultrasound transceiver portion are displayed, the display device matches a scale of the endoscope image with a scale of an ultrasound image and simultaneously displays the endoscope image and the ultrasound image side by side on the display screen, and the display device disposes the endoscope image and the ultrasound image on the display screen such that a point in the endoscope image indicating a predetermined position in the living body matches a point in the ultrasound image indicating the predetermined position on the display screen.

In the blood vessel harvesting system according to one aspect of the present invention, the ultrasound transceiver portion may irradiate a side of the separating portion with respect to a normal line of the outer peripheral surface extending from the ultrasound transceiver portion with the ultrasonic wave.

In the blood vessel harvesting system according to one aspect of the present invention, the display device may display an arc-shaped line having a radius of a predetermined size centered on a blood vessel in the ultrasound image in the endoscope image as a separating position guideline.

In the blood vessel harvesting system according to one aspect of the present invention, the blood vessel harvesting system further includes an input device that receives an input operation by an operator of the blood vessel harvesting system, in which the input device may include a separating position guideline radius setting unit that receives an input of a set value of a radius of the separating position guideline, and the display device may display the separating position guideline having the radius of the set value input to the separating position guideline radius setting unit in the endoscope image.

In the blood vessel harvesting system according to one aspect of the present invention, the separating device may further include an acoustic medium supply portion that supplies physiological saline as an acoustic medium into a living body.

In the blood vessel harvesting system according to one aspect of the present invention, the blood vessel harvesting system may further include a blood vessel pressurizing device that applies pressure into a blood vessel to be harvested during a period in which the display device displays the ultrasound image on the display screen. The blood vessel pressurizing device is preferably pressurized to such an extent that blood flows with arterial pressure from a line punctured into an artery, for example, in order to avoid damage to the vascular endothelium due to applying pressure into the blood vessel.

In the blood vessel harvesting system according to one aspect of the present invention, the blood vessel harvesting system further includes a dissection device that performs hemostasis and cutting of a side branch extending radially from an outer peripheral surface of the blood vessel to be harvested, in which the dissection device may include a clip processing unit that performs the hemostasis of the side branch and a scissors portion that performs the cutting of the side branch.

According to the present invention, it is possible to provide a blood vessel harvesting system capable of grasping a position of a blood vessel covered with a surrounding tissue when operating a separating device.

DETAILED DESCRIPTION

Hereinafter, embodiments of the blood vessel harvesting system of the present invention will be described with reference to the drawings.

Figure 1:
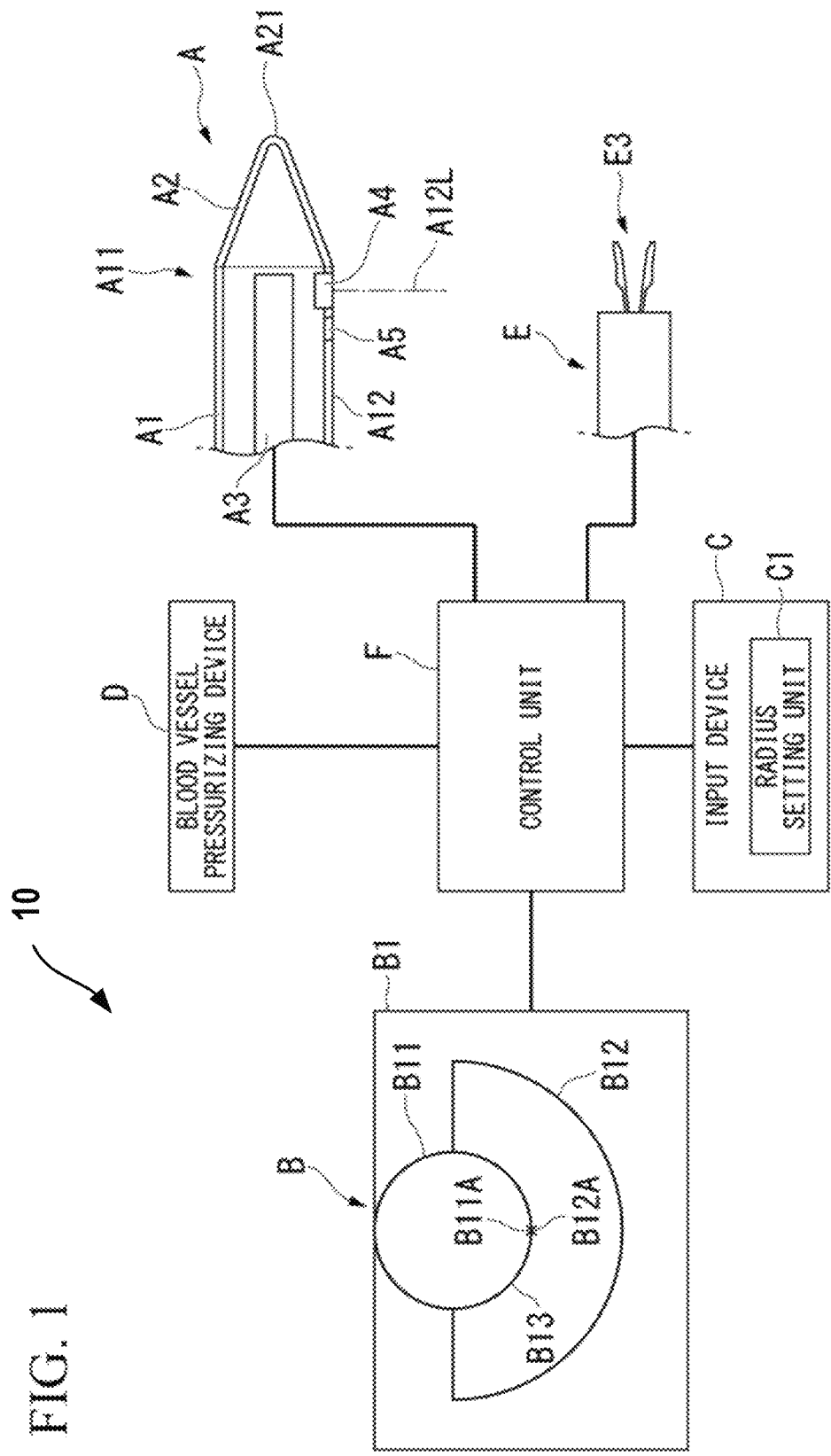
FIG. 1 is a diagram showing an example of a configuration of the blood vessel harvesting system of the first embodiment.
Figure 2:
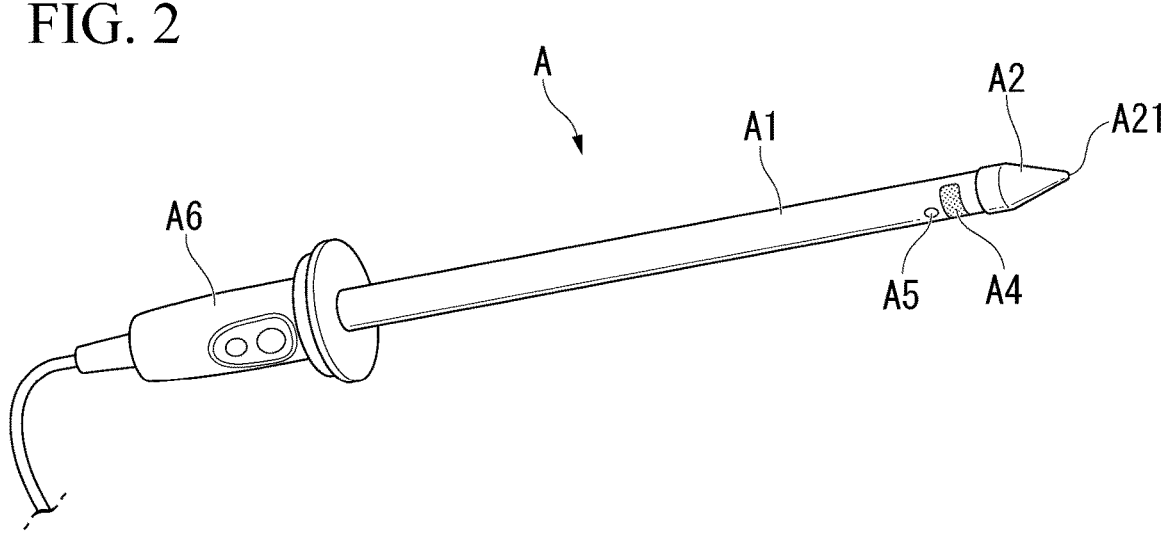
FIG. 2 is a diagram showing an example of an overall configuration of the separating device shown in FIG. 1.

FIG. 1 is a diagram showing an example of a configuration of a blood vessel harvesting system 10 of the first embodiment. FIG. 2 is a diagram showing an example of an overall configuration of a separating device A shown in FIG. 1.

In the example shown in FIGS. 1 and 2, the blood vessel harvesting system 10 of the first embodiment is used to harvest a blood vessel GR (refer to FIG. 3) to be used as a substitute blood vessel such as a great saphenous vein graft, or the like, in a state of being covered with a surrounding tissue SR (refer to FIG. 3) having a uniform thickness. The blood vessel harvesting system 10 includes the separating device A, a display device B, an input device C, a blood vessel pressurizing device D, a dissection device E, and a control unit F.

The separating device A separates the surrounding tissue SR from the blood vessel GR and the like. The separating device A includes a rod portion A1, a separating portion A2, an endoscope portion A3, an ultrasound transceiver portion A4, an acoustic medium supply portion A5, and a grip portion A6.

The rod portion A1 is a part inserted into an interior IV of the living body (refer to FIG. 3) from a small incision in the skin.

In the example shown in FIGS. 1 and 2, the rod portion A1 has a substantially cylindrical shape (has a circular cross-sectional shape), but in other examples, a rod A1 may have a flat shape, for example, similarly to the base portion of the JP2017153606A (may have an elliptical cross-sectional shape).

In the example shown in FIGS. 1 and 2, the separating portion A2 is formed in a tapered shape (for example, a substantially conical shape) by an optically transparent material. The separating portion A2 is disposed at the distal end part A11 of the rod portion A1. The separating portion A2 includes a top portion A21.

The endoscope portion A3 is disposed inside the rod portion A1. The endoscope portion A3 captures an endoscope image B11 of an interior of a living body via the separating portion A2. The endoscope portion A3 is an imaging device for an endoscope. The endoscope portion A3 includes an illumination portion (not shown) for irradiating the interior IV of the living body with illumination light, and a camera portion (not shown) for capturing an image (endoscope image B11) of the interior IV of the living body illuminated by the illumination light. The top portion A21 of the separating portion A2 is disposed on, for example, a central axis (optical axis) of the camera portion.

The ultrasound transceiver portion A4 is disposed on an outer peripheral surface A12 of the rod portion A1. The ultrasound transceiver portion A4 includes an oscillator unit (not shown) that irradiates the interior IV of the living body with an ultrasonic wave US (refer to FIG. 3) and receives the reflected wave from the interior IV of living body.

Figure 3:
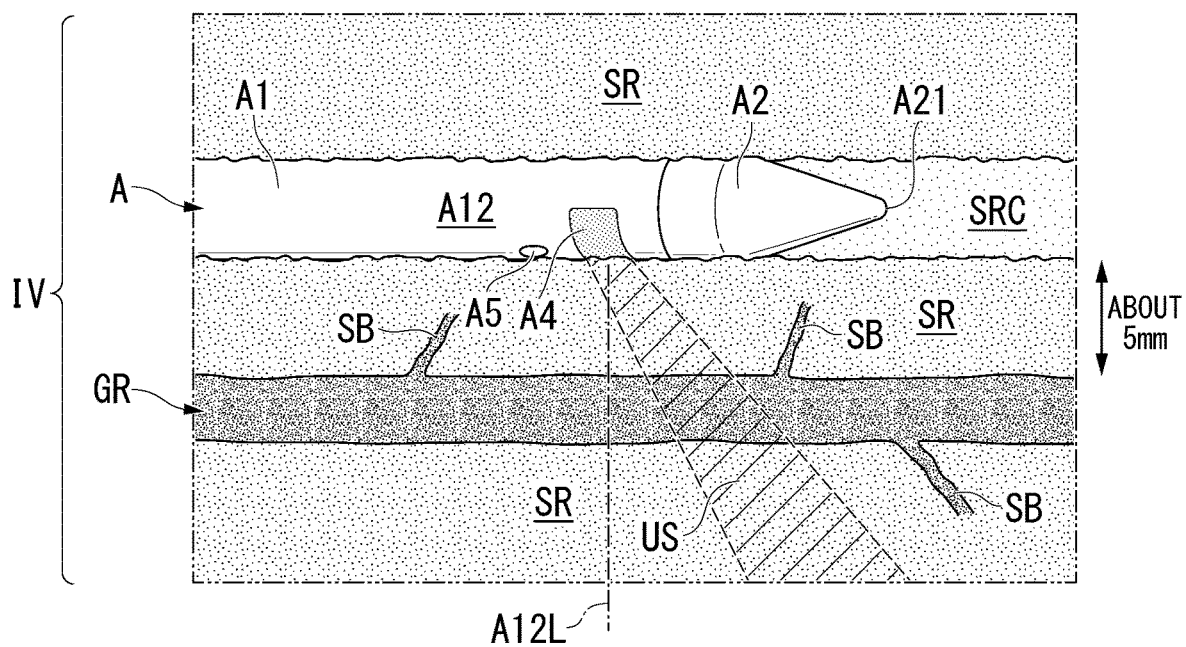
FIG. 3 is a diagram showing an example of an irradiation direction of an ultrasonic wave irradiated from an ultrasound transceiver portion.

FIG. 3 is a diagram showing an example of an irradiation direction of an ultrasonic wave US irradiated from an ultrasound transceiver portion A4.

In the example shown in FIG. 3, the irradiation direction of the ultrasonic wave US irradiated from the ultrasound transceiver portion A4 is set to an advancing direction (right side of FIG. 3) of the separating device A by, for example, an acoustic lens (not shown). More specifically, the ultrasound transceiver portion A4 irradiates a side (right side of FIG. 3) of the separating portion A2 with respect to a normal line A12L of the outer peripheral surface A12 of the rod portion A1 extending from the ultrasound transceiver portion A4 with the ultrasonic wave US.

In FIG. 3, SB indicates a side branch extending radially from an outer peripheral surface of the blood vessel GR to be harvested. SRC indicates a cavity formed in the interior IV of the living body by the separating portion A2 separating the surrounding tissue SR of the blood vessel GR.

In the example shown in FIG. 3, as described above, the ultrasound transceiver portion A4 irradiates the side of the separating portion A2 with respect to the normal line A12L of the outer peripheral surface A12 of the rod portion A1 extending from the ultrasound transceiver portion A4 with the ultrasonic wave US, but in other examples, the ultrasound transceiver portion A4 may irradiate a direction different from that of the example shown in FIG. 3 with the ultrasonic wave US.

In the example shown in FIGS. 1 and 2, the acoustic medium supply portion A5 supplies, for example, physiological saline, as an acoustic medium to which the ultrasonic wave US irradiated from the ultrasound transceiver portion A4 propagates, to the interior IV of living body. The grip portion A6 is gripped by an operator of the separating device A.

In another example, the separating device A may not include the acoustic medium supply portion A5.

In the example shown in FIGS. 1 and 2, the control unit F generates an ultrasound image B12 of the interior IV of the living body based on the reflected wave from the interior IV of the living body received by the ultrasound transceiver portion A4. Specifically, the control unit F generates the ultrasound image B12 of the interior IV of the living body by performing processing such as luminance modulation for the reflected wave from the interior IV of living body.

The display device B displays the endoscope image B11 captured by the endoscope portion A3 and the ultrasound image B12 generated by the control unit F. The display device B includes a display screen B1 on which the endoscope image B11 and the ultrasound image B12 are displayed. In addition, the display device B displays a boundary line B13 between the endoscope image B11 and the ultrasound image B12 on the display screen B1.

The operator of the separating device A can grasp a position, a direction, and the like of the surrounding tissue SR to be separated by the separating portion A2 by viewing the endoscope image B11 displayed on the display screen B1. The operator of the separating device A can proceed with separation processing while grasping a position of the blood vessel GR and the side branch SB and a thickness of the surrounding tissue SR to be left in the state of adhering to the blood vessel GR by viewing the ultrasound image B11 and the endoscope image B12 displayed on the display screen B1.

Figure 4:
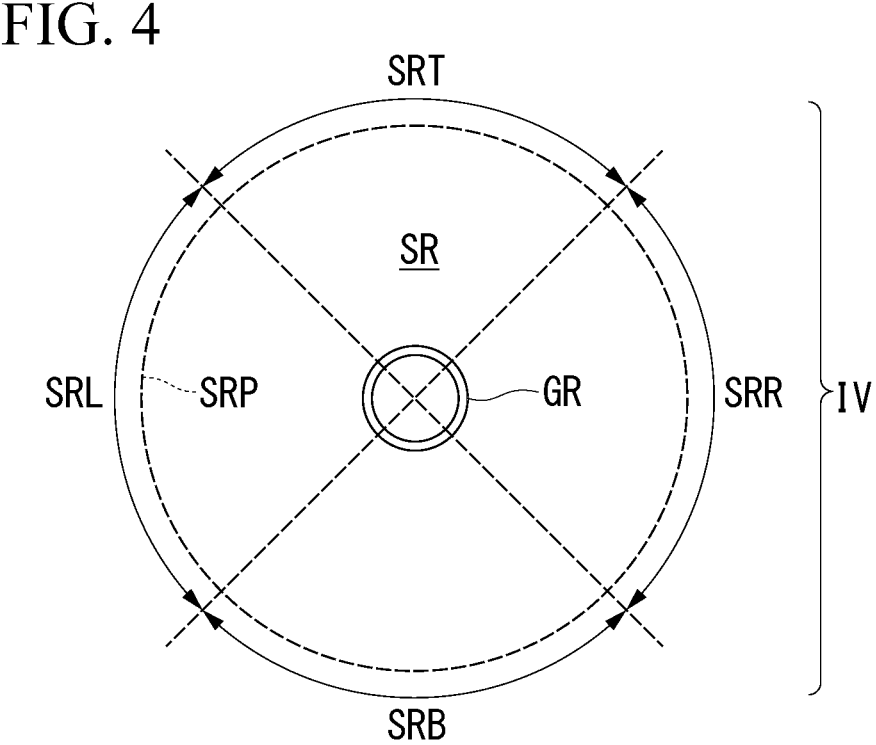
FIG. 4 is a diagram explaining an example of a separating position set for harvesting a blood vessel in a state of being covered with a surrounding tissue having a uniform thickness.

FIG. 4 is a diagram explaining an example of a separating position SRP set for harvesting a blood vessel GR in a state of being covered with a surrounding tissue SR having a uniform thickness.

In the example shown in FIG. 4, in order to harvest the blood vessel GR in a state of being covered with the surrounding tissue SR having a uniform thickness (for example, a thickness of 5 mm), the separating position SRP, which is a position at which the surrounding tissue SR is separated by the separating portion A2 of the separating device A, is set on a cylindrical surface centered on the blood vessel GR.

In FIG. 4, the SRT indicates an upper part of the separating position SRP of the surrounding tissue SR, which is positioned above the blood vessel GR. The SRB indicates a lower part of the separating position SRP of the surrounding tissue SR, which is positioned below the blood vessel GR. The SRL indicates a left part of the separating position SRP of the surrounding tissue SR, which is positioned on the left side of the blood vessel GR. The SRR indicates a right part of the separating position SRP of the surrounding tissue SR, which is positioned on the right side of the blood vessel GR.

Figure 5A:
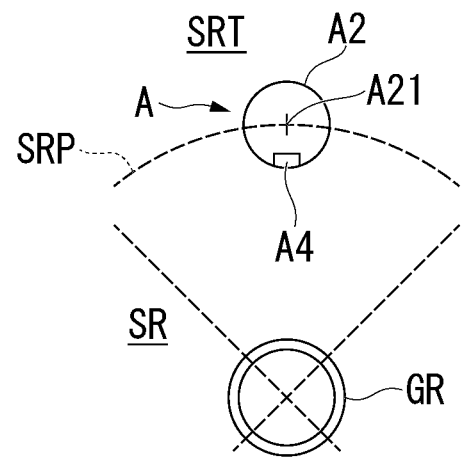
FIG. 5A is a diagram showing an example of a relationship between a blood vessel and an ultrasound transceiver portion of a separating device when an upper part of a surrounding tissue is separated at a separating position by the separating portion of the separating device.

FIG. 5A is a diagram showing an example of a relationship between a blood vessel GR and an ultrasound transceiver portion A4 of a separating device A when an upper part SRT of a surrounding tissue SR is separated at a separating position SRP by the separating portion A2 of the separating device A.

In the example shown in FIG. 5A, when the upper part SRT of the surrounding tissue SR is separated at the separating position SRP by the separating portion A2 of the separating device A, the separating device A is operated by the operator of the separating device A such that the ultrasound transceiver portion A4 is positioned below the top portion A21 of the separating portion A2 and faces the blood vessel GR.

Figure 6A:
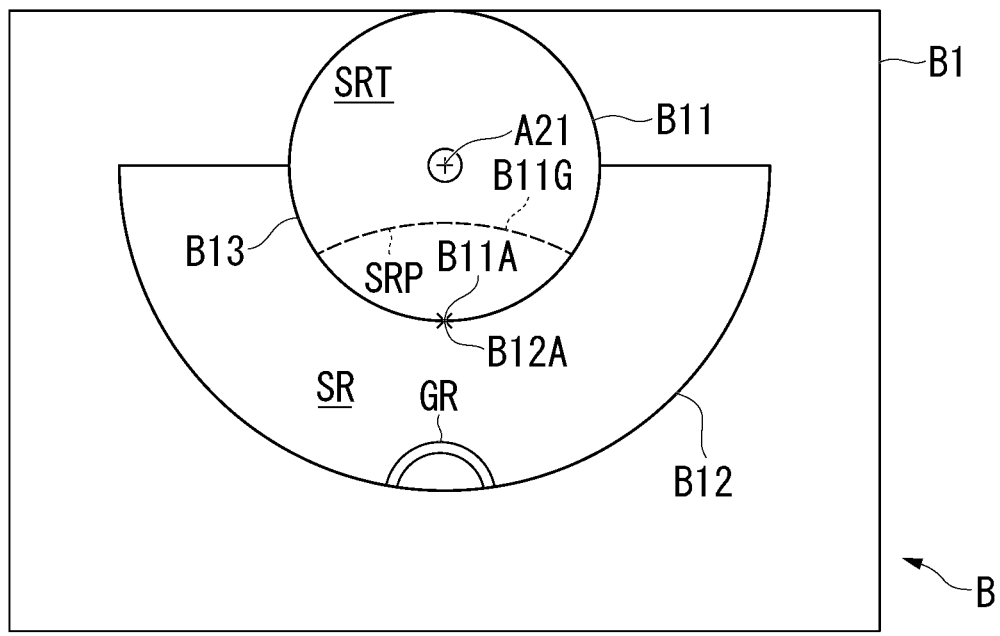
FIG. 6A is a diagram showing an example of an endoscope image and an ultrasound image displayed on a display screen of a display device when an operation for positioning the separating portion of the separating device at the separating position of the upper part of the surrounding tissue shown in FIG. 5A is performed.

FIG. 6A is a diagram showing an example of an endoscope image B11 and an ultrasound image B12 displayed on a display screen B1 of a display device B when an operation for positioning the separating portion A2 of the separating device A at the separating position SRP of the upper part SRT of the surrounding tissue SR shown in FIG. 5A is performed.

In the example shown in FIGS. 1 and 6A, the display device B matches a scale of the endoscope image B11 with a scale of the ultrasound image B12, and simultaneously displays the endoscope image B11 and the ultrasound image B12 side by side on the display screen B1. In addition, the display device B disposes the endoscope image B11 and the ultrasound image B12 on the display screen B1 such that a point B11A in the endoscope image B11 indicating a predetermined position in the interior IV of the living body and a point B12A in the ultrasound image B12 indicating the predetermined position match with each other on the display screen B1.

More specifically, in the example shown in FIG. 6A, the top portion A21 of the separating portion A2 disposed on the central axis (optical axis) of the camera portion of the endoscope portion A3 of the separating device A and the blood vessel GR covered with the surrounding tissue SR are simultaneously displayed on the display screen B1 of the display device B. Therefore, the operator of the separating device A can perform separation processing of the upper part SRT of the surrounding tissue SR by the separating portion A2 while grasping a position of the blood vessel GR covered with the surrounding tissue SR (that is, while grasping a distance between the blood vessel GR and the separating portion A2 of the separating device A).

That is, in the example shown in FIG. 6A, the operator of the separating device A can make a thickness of the upper part SRT of the surrounding tissue SR covering the upper part of the outer peripheral surface of the blood vessel GR to be harvested uniform by operating the separating device A while grasping a position of the blood vessel GR covered with the surrounding tissue SR.

In the example shown in FIGS. 1 and 6A, the display device B displays an arc-shaped line having a radius of a predetermined size centered on a blood vessel GR in the ultrasound image B12 in the endoscope image B11 as a separating position guideline B11G.

In another example, the separating position guideline B11G may not be displayed in the endoscope image B11.

In the example shown in FIG. 6A, the top portion A21 of the separating portion A2 (refer to FIGS. 1 and 2) displayed in the endoscope image B11 is positioned above the separating position guideline B11G. Therefore, the operator of the separating device A can grasp that it is necessary to move the separating portion A2 downward to perform the separation processing of the upper part SRT of the surrounding tissue SR by the separating portion A2.

Figure 5B:
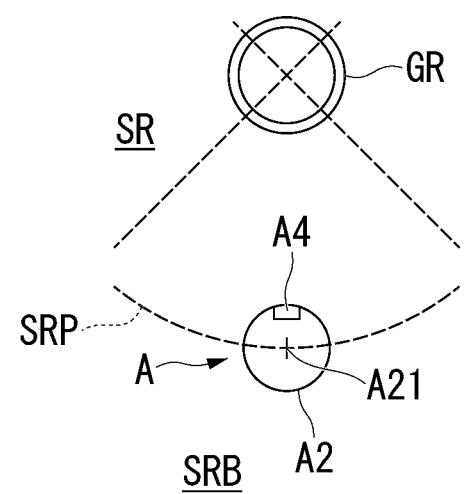
FIG. 5B is a diagram showing an example of a relationship between a blood vessel and an ultrasound transceiver portion of a separating device when a lower part of a surrounding tissue is separated at a separating position by the separating portion of the separating device.

FIG. 5B is a diagram showing an example of a relationship between a blood vessel GR and an ultrasound transceiver portion A4 of a separating device A when a lower part SRB of a surrounding tissue SR is separated at a separating position SRP by the separating portion A2 of the separating device A.

In the example shown in FIG. 5B, when the lower part SRB of the surrounding tissue SR is separated at the separating position SRP by the separating portion A2 of the separating device A, the separating device A is operated by the operator of the separating device A such that the ultrasound transceiver portion A4 is positioned above the top portion A21 of the separating portion A2 and faces the blood vessel GR.

Figure 6B:
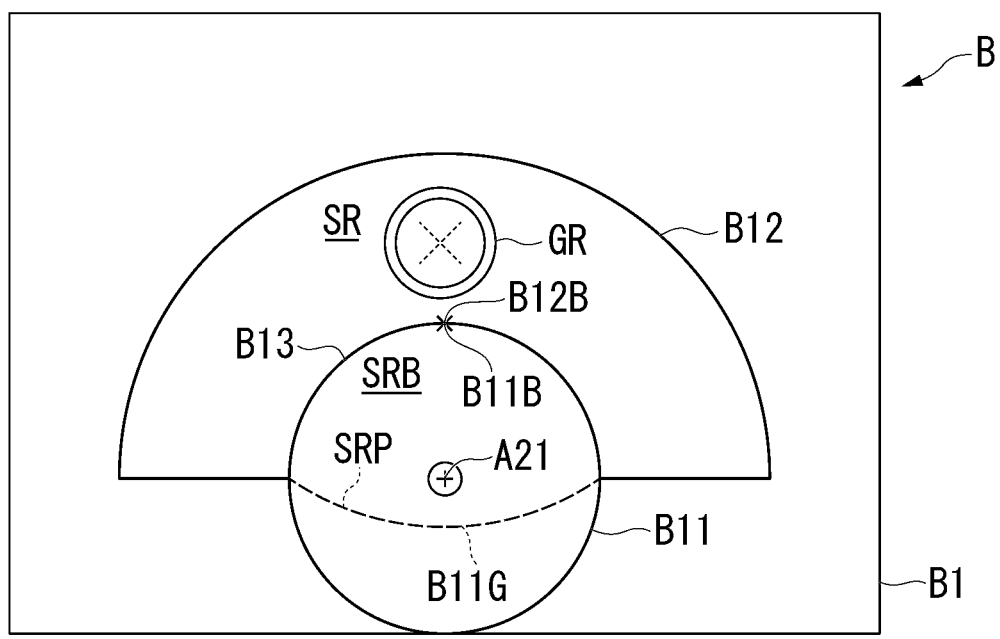
FIG. 6B is a diagram showing an example of an endoscope image and an ultrasound image displayed on a display screen of a display device when an operation for positioning the separating portion of the separating device at the separating position of the lower part of the surrounding tissue shown in FIG. 5B is performed.

FIG. 6B is a diagram showing an example of an endoscope image B11 and an ultrasound image B12 displayed on a display screen B1 of a display device B when an operation for positioning the separating portion A2 of the separating device A at the separating position SRP of the lower part SRB of the surrounding tissue SR shown in FIG. 5B is performed.

In the example shown in FIGS. 1 and 6B, similarly to the example shown in FIG. 6A, the display device B matches a scale of the endoscope image B11 with a scale of the ultrasound image B12, and simultaneously displays the endoscope image B11 and the ultrasound image B12 side by side on the display screen B1. In addition, the display device B disposes the endoscope image B11 and the ultrasound image B12 on the display screen B1 such that a point B11B in the endoscope image B11 indicating a predetermined position in the interior IV of the living body and a point B12B in the ultrasound image B12 indicating the predetermined position match with each other on the display screen B1.

More specifically, in the example shown in FIG. 6B, the top portion A21 of the separating portion A2 disposed on the central axis (optical axis) of the camera portion of the endoscope portion A3 of the separating device A and the blood vessel GR covered with the surrounding tissue SR are simultaneously displayed on the display screen B1 of the display device B. Therefore, the operator of the separating device A can perform separation processing of the lower part SRB of the surrounding tissue SR by the separating portion A2 while grasping a position of the blood vessel GR covered with the surrounding tissue SR (that is, while grasping a distance between the blood vessel GR and the separating portion A2 of the separating device A).

That is, in the example shown in FIG. 6B, the operator of the separating device A can make a thickness of the lower part SRB of the surrounding tissue SR covering the lower part of the outer peripheral surface of the blood vessel GR to be harvested uniform by operating the separating device A while grasping a position of the blood vessel GR covered with the surrounding tissue SR.

In addition, in the example shown in FIGS. 1 and 6B, similarly to the example shown in FIG. 6A, the display device B displays an arc-shaped line having a radius of a predetermined size centered on a blood vessel GR in the ultrasound image B12 in the endoscope image B11 as a separating position guideline B11G.

In another example, the separating position guideline B11G may not be displayed in the endoscope image B11.

In the example shown in FIG. 6B, the top portion A21 of the separating portion A2 (refer to FIGS. 1 and 2) displayed in the endoscope image B11 is positioned above the separating position guideline B11G. Therefore, the operator of the separating device A can grasp that it is necessary to move the separating portion A2 downward to perform the separation processing of the lower part SRB of the surrounding tissue SR by the separating portion A2.

Figure 5C:
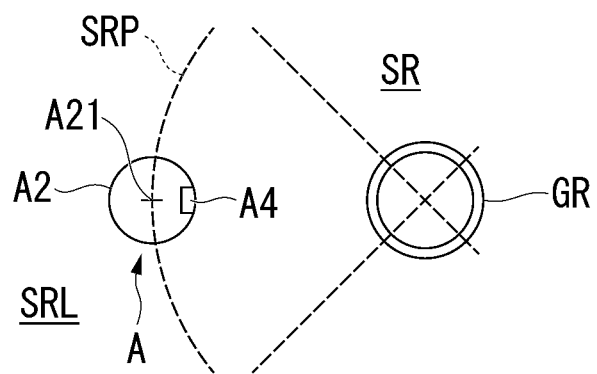
FIG. 5C is a diagram showing an example of a relationship between a blood vessel and an ultrasound transceiver portion of a separating device when a left part of a surrounding tissue is separated at a separating position by the separating portion of the separating device.

FIG. 5C is a diagram showing an example of a relationship between a blood vessel GR and an ultrasound transceiver portion A4 of a separating device A when a left part SRL of a surrounding tissue SR is separated at a separating position SRP by the separating portion A2 of the separating device A.

In the example shown in FIG. 5C, when the left part SRL of the surrounding tissue SR is separated at the separating position SRP by the separating portion A2 of the separating device A, the separating device A is operated by the operator of the separating device A such that the ultrasound transceiver portion A4 is positioned on the right side of the top portion A21 of the separating portion A2 and faces the blood vessel GR.

Figure 6C:
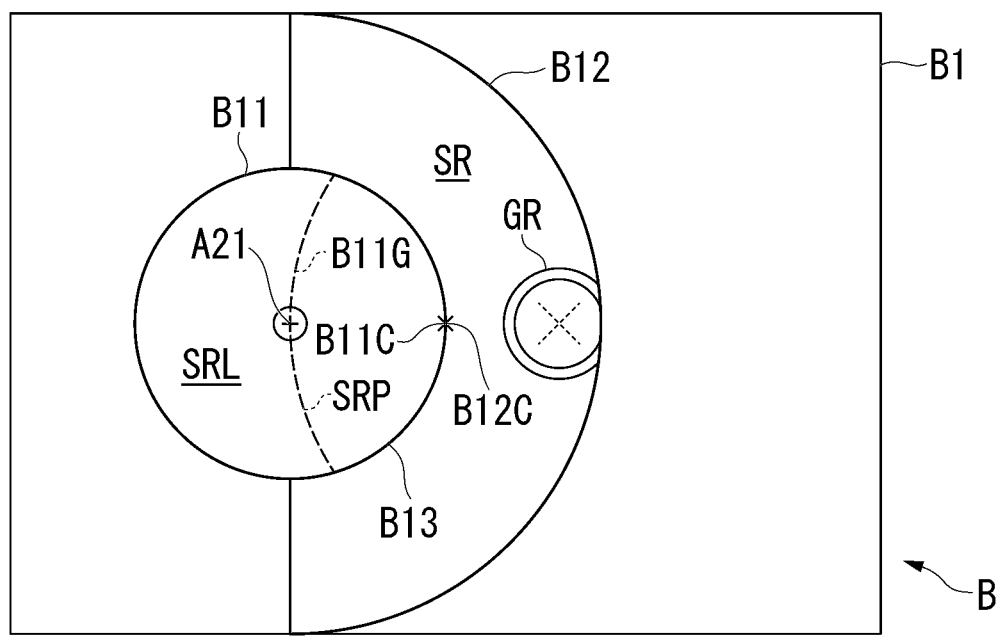
FIG. 6C is a diagram showing an example of an endoscope image and an ultrasound image displayed on a display screen of a display device when an operation for positioning the separating portion of the separating device at the separating position of the left part of the surrounding tissue shown in FIG. 5C is performed.

FIG. 6C is a diagram showing an example of an endoscope image B11 and an ultrasound image B12 displayed on a display screen B1 of a display device B when an operation for positioning the separating portion A2 of the separating device A at the separating position SRP of the left part SRL of the surrounding tissue SR shown in FIG. 5C is performed.

In the example shown in FIGS. 1 and 6C, similarly to the example shown in FIG. 6A, the display device B matches a scale of the endoscope image B11 with a scale of the ultrasound image B12, and simultaneously displays the endoscope image B11 and the ultrasound image B12 side by side on the display screen B1. In addition, the display device B disposes the endoscope image B11 and the ultrasound image B12 on the display screen B1 such that a point B11C in the endoscope image B11 indicating a predetermined position in the interior IV of the living body and a point B12C in the ultrasound image B12 indicating the predetermined position match with each other on the display screen B1.

More specifically, in the example shown in FIG. 6C, the top portion A21 of the separating portion A2 disposed on the central axis (optical axis) of the camera portion of the endoscope portion A3 of the separating device A and the blood vessel GR covered with the surrounding tissue SR are simultaneously displayed on the display screen B1 of the display device B. Therefore, the operator of the separating device A can perform separation processing of the left part SRL of the surrounding tissue SR by the separating portion A2 while grasping a position of the blood vessel GR covered with the surrounding tissue SR (that is, while grasping a distance between the blood vessel GR and the separating portion A2 of the separating device A).

That is, in the example shown in FIG. 6C, the operator of the separating device A can make a thickness of the left part SRL of the surrounding tissue SR covering the left part of the outer peripheral surface of the blood vessel GR to be harvested uniform by operating the separating device A while grasping a position of the blood vessel GR covered with the surrounding tissue SR.

In addition, in the example shown in FIGS. 1 and 6C, similarly to the example shown in FIG. 6A, the display device B displays an arc-shaped line having a radius of a predetermined size centered on a blood vessel GR in the ultrasound image B12 in the endoscope image B11 as a separating position guideline B11G.

In another example, the separating position guideline B11G may not be displayed in the endoscope image B11.

In the example shown in FIG. 6C, the top portion A21 of the separating portion A2 (refer to FIGS. 1 and 2) displayed in the endoscope image B11 is positioned on the separating position guideline B11G. Therefore, the operator of the separating device A can understand that the separation processing of the left part SRL of the surrounding tissue SR should be performed by the separating portion A2 at a current position.

Figure 5D:
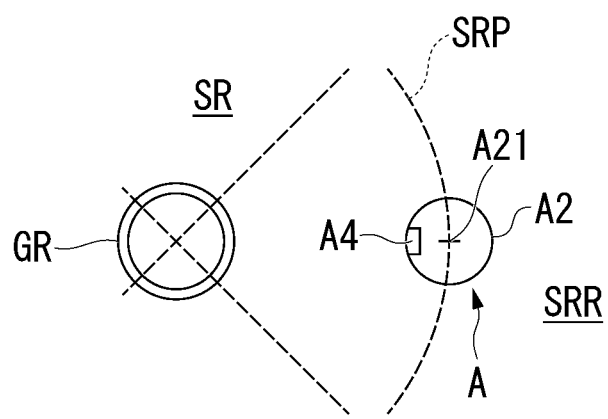
FIG. 5D is a diagram showing an example of a relationship between a blood vessel and an ultrasound transceiver portion of a separating device when a right part of a surrounding tissue is separated at a separating position by the separating portion of the separating device.

FIG. 5D is a diagram showing an example of a relationship between a blood vessel GR and an ultrasound transceiver portion A4 of a separating device A when a right part SRR of a surrounding tissue SR is separated at a separating position SRP by the separating portion A2 of the separating device A.

In the example shown in FIG. 5D, when the right part SRR of the surrounding tissue SR is separated at the separating position SRP by the separating portion A2 of the separating device A, the separating device A is operated by the operator of the separating device A such that the ultrasound transceiver portion A4 is positioned on the left side of the top portion A21 of the separating portion A2 and faces the blood vessel GR.

Figure 6D:
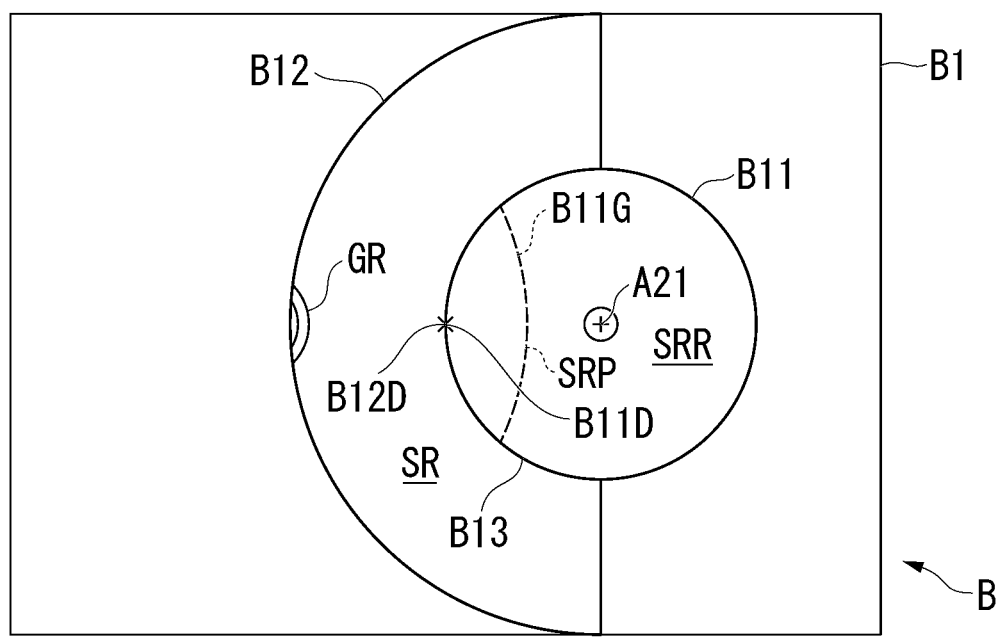
FIG. 6D is a diagram showing an example of an endoscope image and an ultrasound image displayed on a display screen of a display device when an operation for positioning the separating portion of the separating device at the separating position of the right part of the surrounding tissue shown in FIG. 5D is performed.

FIG. 6D is a diagram showing an example of an endoscope image B11 and an ultrasound image B12 displayed on a display screen B1 of a display device B when an operation for positioning the separating portion A2 of the separating device A at the separating position SRP of the right part SRR of the surrounding tissue SR shown in FIG. 5D is performed.

In the example shown in FIGS. 1 and 6D, similarly to the example shown in FIG. 6A, the display device B matches a scale of the endoscope image B11 with a scale of the ultrasound image B12, and simultaneously displays the endoscope image B11 and the ultrasound image B12 side by side on the display screen B1. In addition, the display device B disposes the endoscope image B11 and the ultrasound image B12 on the display screen B1 such that a point B11D in the endoscope image B11 indicating a predetermined position in the interior IV of the living body and a point B12D in the ultrasound image B12 indicating the predetermined position match with each other on the display screen B1.

More specifically, in the example shown in FIG. 6D, the top portion A21 of the separating portion A2 disposed on the central axis (optical axis) of the camera portion of the endoscope portion A3 of the separating device A and the blood vessel GR covered with the surrounding tissue SR are simultaneously displayed on the display screen B1 of the display device B. Therefore, the operator of the separating device A can perform separation processing of the right part SRR of the surrounding tissue SR by the separating portion A2 while grasping a position of the blood vessel GR covered with the surrounding tissue SR (that is, while grasping a distance between the blood vessel GR and the separating portion A2 of the separating device A).

That is, in the example shown in FIG. 6D, the operator of the separating device A can make a thickness of the right part SRR of the surrounding tissue SR covering the right part of the outer peripheral surface of the blood vessel GR to be harvested uniform by operating the separating device A while grasping a position of the blood vessel GR covered with the surrounding tissue SR.

In addition, in the example shown in FIGS. 1 and 6D, similarly to the example shown in FIG. 6A, the display device B displays an arc-shaped line having a radius of a predetermined size centered on a blood vessel GR in the ultrasound image B12 in the endoscope image B11 as a separating position guideline B11G.

In another example, the separating position guideline B11G may not be displayed in the endoscope image B11.

In the example shown in FIG. 6D, the top portion A21 of the separating portion A2 (refer to FIGS. 1 and 2) displayed in the endoscope image B11 is positioned on the right side of the separating position guideline B11G. Therefore, the operator of the separating device A can grasp that it is necessary to move the separating portion A2 to the left side to perform the separation processing of the right part SRR of the surrounding tissue SR by the separating portion A2.

In the example shown in FIG. 1, the input device C receives an input operation of the operator of the blood vessel harvesting system 10. The input device C includes a radius setting unit C1. The radius setting unit C1 receives, for example, an input of a set value of a radius of the separating position guideline B11G (refer to FIG. 6A and the like) by the operator of the separating device A.

In another example, the input device C may not include the radius setting unit C1.

Figure 7A:
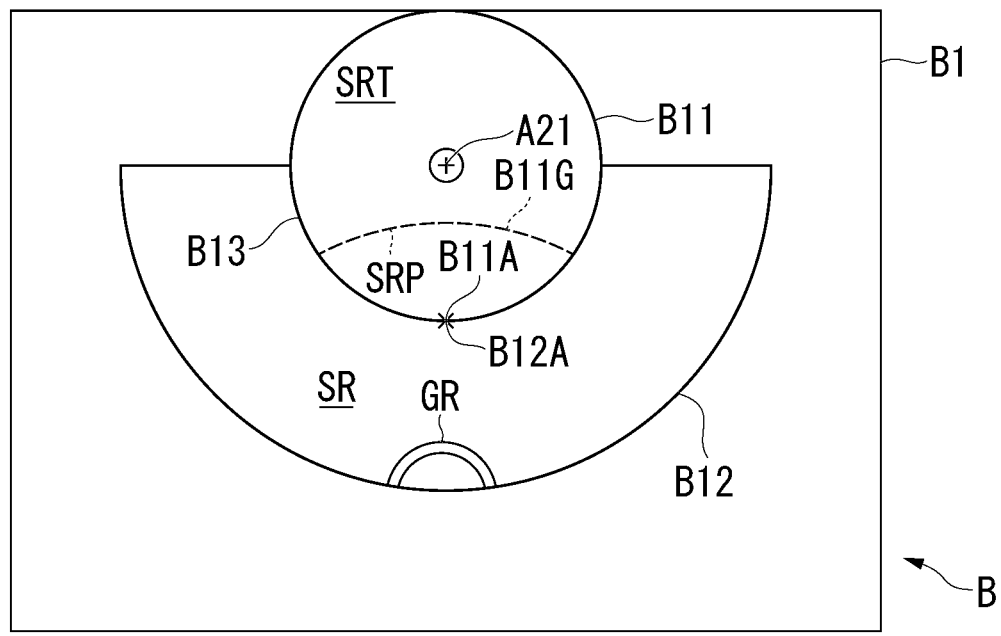
FIG. 7A is a diagram showing an example of an endoscope image and an ultrasound image displayed on a display screen of a display device when a radius of a separating position guideline is set to the first set value.
Figure 7B:
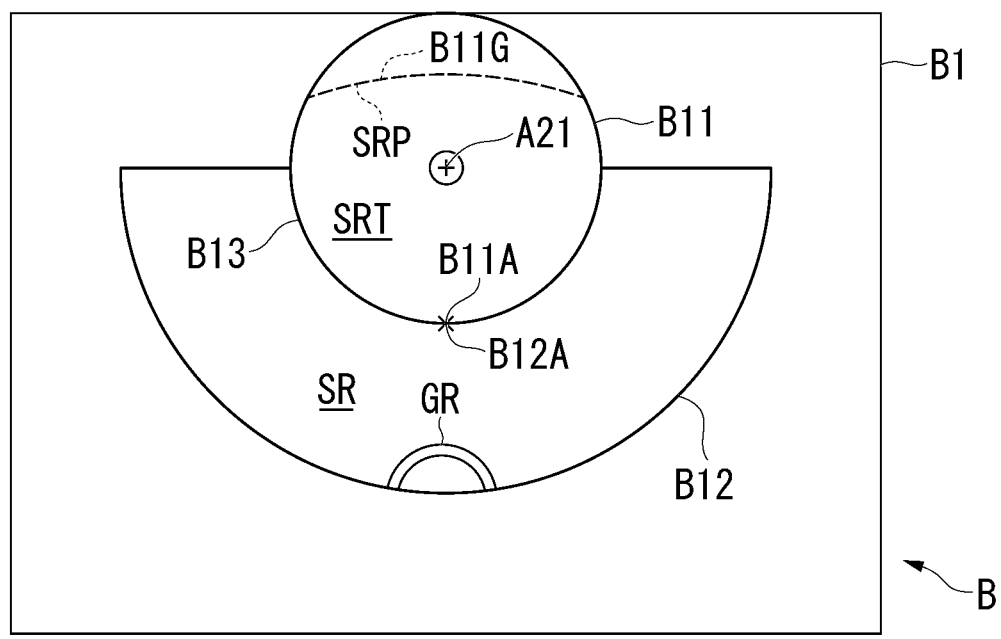
FIG. 7B is a diagram showing an example of an endoscope image and an ultrasound image displayed on a display screen of a display device when a radius of a separating position guideline is set to the second set value (>the first set value).

FIG. 7A is a diagram showing an example of an endoscope image B11 and an ultrasound image B12 displayed on a display screen B1 of a display device B when a radius of a separating position guideline B11G is set to the first set value. FIG. 7B is a diagram showing an example of an endoscope image B11 and an ultrasound image B12 displayed on a display screen B1 of a display device B when a radius of a separating position guideline B11G is set to the second set value (>the first set value).

In the example shown in FIGS. 1 and 7A, the radius of the separating position guideline B11G is set to the first set value via the radius setting unit C1 of the input device C. The display device B displays the separating position guideline B11G having the radius of the first set value input to the radius setting unit C1 in the endoscope image B11. Therefore, the operator of the separating device A can grasp that it is necessary to move the separating portion A2 to the lower side (lower side of FIG. 7A) in order to harvest the blood vessel GR in a state of being covered with the surrounding tissue SR having a substantially cylindrical shape and the radius of the first set value.

In the example shown in FIGS. 1 and 7B, the radius of the separating position guideline B11G is set to the second set value (>the first set value) via the radius setting unit C1 of the input device C. The display device B displays the separating position guideline B11G having the radius of the second set value input to the radius setting unit C1 in the endoscope image B11. Therefore, the operator of the separating device A can grasp that it is necessary to move the separating portion A2 to the upper side (upper side of FIG. 7B) in order to harvest the blood vessel GR in a state of being covered with the surrounding tissue SR having a substantially cylindrical shape and the radius of the second set value.

In the example shown in FIG. 1, the blood vessel pressurizing device D applies pressure into the blood vessel GR to be harvested during a period in which the display device B displays the ultrasound image B12 on the display screen B1. For example, when the great saphenous vein graft is to be harvested, in order to improve the visibility of the great saphenous vein graft in the ultrasound image B12, cannulation is performed at the wound, and blood applied with arterial pressure flows into the great saphenous vein graft by connecting a catheter extended from a sheath placed in the femoral artery.

In another example, the blood vessel harvesting system 10 may not include the blood vessel pressurizing device D.

In the example shown in FIG. 1, the dissection device E includes a hemostatic and cutting processing unit E3 that performs hemostasis and cutting (side branch processing) of the side branch SB (refer to FIG. 3). The hemostatic and cutting processing unit E3 includes, for example, a pair of electrodes having a bipolar structure.

Since the side branch SB having a certain thickness is displayed on the ultrasound image B12 even when it is embedded in the surrounding tissue SR, the operator of the separating device A can grasp the side branch SB requiring hemostatic and cutting processing before the side branch SB appears on the endoscope image by viewing the ultrasound image B12 displayed on the display screen B1. This reduces the appearance of an unexpected side branch SB and reduces damage to the side branch SB and blood vessel GR.

In the blood vessel harvesting system 10 of the first embodiment, as described above, the endoscope image B11 of the interior IV of the living body captured by the endoscope portion A3 and the ultrasound image B12 generated based on the reflected wave received by the ultrasound transceiver portion A4 are displayed simultaneously side by side. Therefore, the operator of the separating device A can proceed with the separation processing of the surrounding tissue SR while viewing the endoscope image B11 while grasping a position of the blood vessel GR covered with the surrounding tissue SR by viewing the ultrasound image B12. As a result, the operator of the separating device A can harvest the blood vessel GR in a state of being covered with the surrounding tissue SR having a uniform thickness.

In addition, in the blood vessel harvesting system 10 of the first embodiment, as described above, the ultrasound transceiver portion A4 irradiates a side (right side of FIG. 3) of the separating portion A2 with respect to a normal line A12L of the outer peripheral surface A12 of the rod portion A1 extending from the ultrasound transceiver portion A4 with the ultrasonic wave US. Therefore, the display device B can display the ultrasound image B12 at a position adjacent to a position included in the endoscope image B11 in the interior IV of living body.

In addition, in the blood vessel harvesting system 10 of the first embodiment, as described above, the display device B displays an arc-shaped line having a radius of a predetermined size centered on a blood vessel GR in the ultrasound image B12 in the endoscope image B11 as a separating position guideline B11G. Therefore, the blood vessel harvesting system 10 can reduce the difficulty of the separation processing of the surrounding tissue SR by the operator of the separating device A as compared with a case where the separating position guideline B11G is not displayed.

In addition, in the blood vessel harvesting system 10 of the first embodiment, as described above, the display device B displays the separating position guideline B11G having the radius of the set value input to the radius setting unit C1 in the endoscope image B11. Therefore, the display device B can display the separating position guideline B11G having a radius of a different size in the endoscope image B11 according to the input of the set value to the radius setting unit C1.

In addition, in the blood vessel harvesting system 10 of the first embodiment, as described above, the acoustic medium supply portion A5 supplies, for example, physiological saline, as an acoustic medium to which the ultrasonic wave US irradiated from the ultrasound transceiver portion A4 propagates, to the interior IV of living body. Therefore, the ultrasound image B12 can be made clearer as compared with a case where the acoustic medium is not supplied to the interior IV of living body.

In the blood vessel harvesting system 10 of the first embodiment, as described above, the blood vessel pressurizing device D applies pressure into the blood vessel GR to be harvested during a period in which the display device B displays the ultrasound image B12 on the display screen B1. Therefore, it is possible to suppress the possibility that the blood vessel GR is crushed during a period in which the display device B displays the ultrasound image B12 on the display screen B1. As a result, the display device B can clearly display the blood vessel GR in the ultrasound image B12 as compared with a case where no pressure is applied in the blood vessel GR to be harvested.

Hereinafter, a second embodiment of the blood vessel harvesting system of the present invention will be described with reference to the drawings.

The blood vessel harvesting system 10 of the second embodiment is configured similarly to the blood vessel harvesting system 10 of the above-described first embodiment, except for the points described later. Accordingly, according to the blood vessel harvesting system 10 of the second embodiment, the same effect as that of the blood vessel harvesting system 10 of the above-described first embodiment described above can be obtained except for the points described later.

Figure 8:
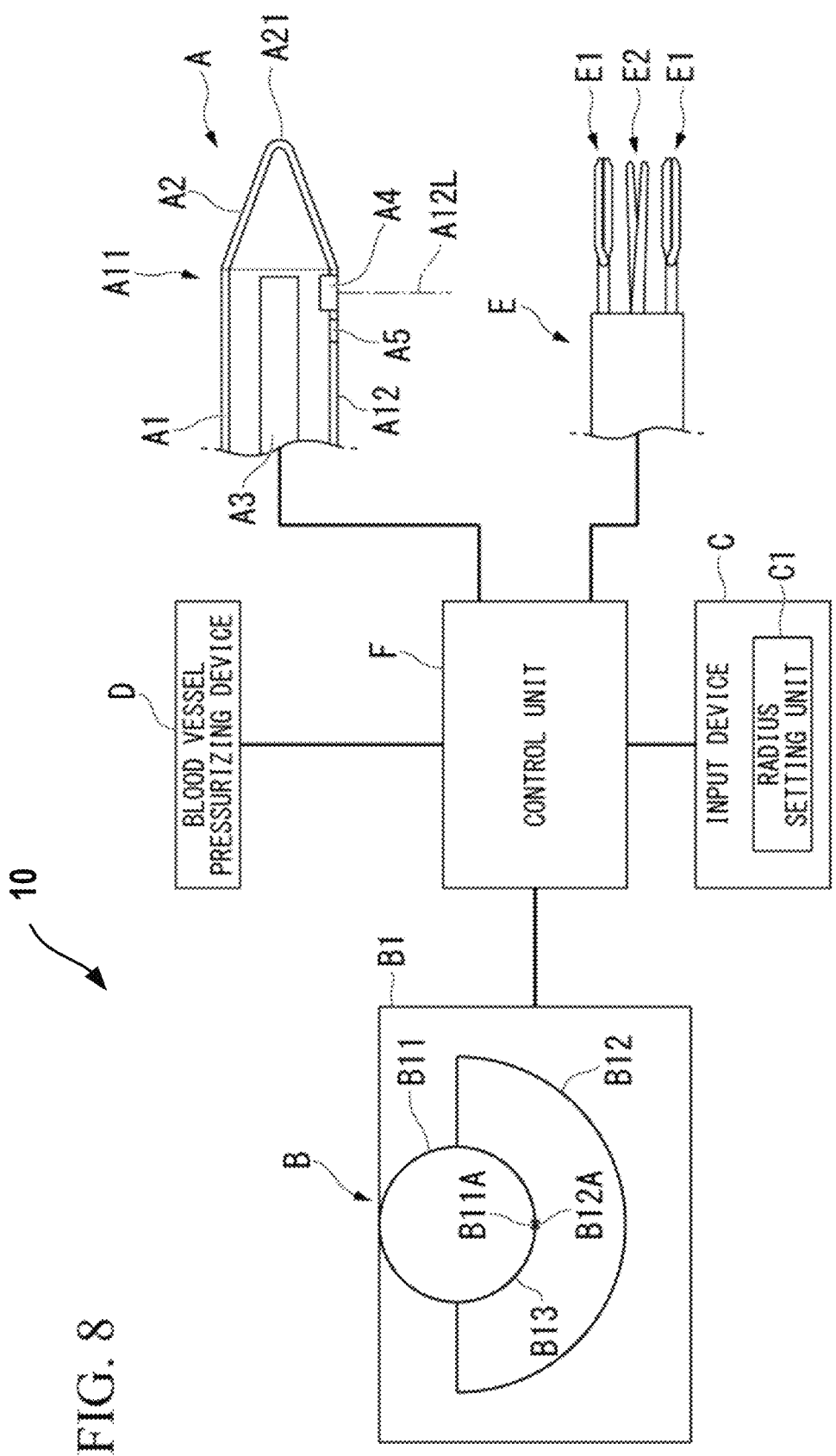
FIG. 8 is a diagram showing an example of a configuration of the blood vessel harvesting system of the second embodiment.

FIG. 8 is a diagram showing an example of a configuration of a blood vessel harvesting system 10 of the second embodiment.

In the example shown in FIG. 1, the dissection device E includes the hemostatic and cutting processing unit E3 that performs hemostasis and cutting (side branch processing) of the side branch SB (refer to FIG. 3), but in the example shown in FIG. 8, the dissection device E includes clip processing units E1 and a scissors portion E2.

In the example shown in FIG. 8, the side branch processing is performed by the clip processing units E1 and the scissors portion E2. Specifically, the clip processing units E1 perform the hemostasis of the side branch SB. The scissors portion E2 performs cutting of the side branch SB in a state in which the hemostasis of the side branch SB is performed by the clip processing units E1 on both sides of the scissors portion E2.

As described above, EVH has advantages in terms of wound complications and cosmetology, but there are also aspects in which problems have been pointed out in terms of graft damage and graft patency rate. On the other hand, the no-touch method is a method that is expected to improve the patency rate of a vein graft, but at present, a harvesting method in which the skin is incised is the mainstream, and there are disadvantages in terms of wound complications and cosmetology. When the no-touch method by EVH can be easily performed with such a new device, it may be possible to obtain advantages in both aspects, which leads to patient benefit, and development.

Both EVH and the no-touch method are not yet widely used in Japan, but EVH is widely used mainly in the United States, and is expected to expand overseas.

As described above, the embodiments of the present invention have been described in detail with reference to the drawings, but the specific configuration is not limited to this embodiment, and modifications may be made as appropriate without departing from the spirit of the present invention. The configurations described in each of the above-described embodiments and examples may be combined.

What is claimed is:

1. A blood vessel harvesting system configured to harvest a blood vessel in a state of being covered with a surrounding tissue, the blood vessel harvesting system comprising:
   a separating device; and
   a display device,
   wherein the separating device includes
   a rod portion configured to be inserted into a living body,
   an optically transparent taper-shaped separating portion configured to be disposed at a distal end part of the rod portion,
   an endoscope portion configured to be disposed inside the rod portion, and capture an endoscope image of an interior of the living body via the separating portion, and
   an ultrasound transceiver portion configured to be disposed on an outer peripheral surface of the rod portion, irradiate the interior of the living body with an ultrasonic wave, and receive a reflected wave from the interior of the living body,
   the display device includes a display screen on which the endoscope image and an ultrasound image generated based on the reflected wave received by the ultrasound transceiver portion are displayed,
   the display device matches a scale of the endoscope image with a scale of an ultrasound image and simultaneously displays the endoscope image and the ultrasound image side by side on the display screen, and
   the display device disposes the endoscope image and the ultrasound image on the display screen in a manner that a point in the endoscope image indicating a predetermined position in the living body matches a point in the ultrasound image indicating the predetermined position on the display screen,
   wherein the ultrasound transceiver portion irradiates a side of the separating portion with respect to a normal line of the outer peripheral surface extending from the ultrasound transceiver portion with the ultrasonic wave, and
   wherein the display device displays an arc-shaped line having a radius of a predetermined size centered on a blood vessel in the ultrasound image in the endoscope image as a separating position guideline.

2. The blood vessel harvesting system according to claim 1, further comprising:
   an input device configured to receive an input operation by an operator of the blood vessel harvesting system,
   wherein the input device includes a separating position guideline radius setting unit configured to receive an input of a set value of a radius of the separating position guideline, and the display device displays the separating position guideline having the radius of the set value input to the separating position guideline radius setting unit in the endoscope image.

3. The blood vessel harvesting system according to claim 1, wherein the separating device further includes an acoustic medium supply portion configured to supply physiological saline as an acoustic medium into the living body.

4. The blood vessel harvesting system according to claim 1, further comprising:
the blood vessel pressurizing device configured to apply pressure into the blood vessel to be harvested during a period in which the display device displays the ultrasound image on the display screen.

5. The blood vessel harvesting system according to claim 1, further comprising:
a dissection device configured to perform hemostasis and cutting of a side branch extending radially from an outer peripheral surface of the blood vessel to be harvested,
wherein the dissection device includes a clip processing unit configured to perform the hemostasis of the side branch and a scissors portion configured to perform the cutting of the side branch.

\* \* \* \* \*